United States Patent
Taghizadeh et al.

(10) Patent No.: US 8,967,512 B1
(45) Date of Patent: *Mar. 3, 2015

(54) SYSTEMS AND METHODS FOR PROCESSING CELLS

(71) Applicant: Auxocell Laboratories, Inc., Cambridge, MA (US)

(72) Inventors: Rouzbeh R. Taghizadeh, Cambridge, MA (US); John Meade, Mendon, MA (US)

(73) Assignee: Auxocell Laboratories, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/547,956

(22) Filed: Nov. 19, 2014

Related U.S. Application Data

(63) Continuation of application No. 13/933,034, filed on Jul. 1, 2013, now Pat. No. 8,893,995, which is a continuation of application No. PCT/US2012/064130, filed on Nov. 8, 2012.

(60) Provisional application No. 61/557,127, filed on Nov. 8, 2011.

(51) Int. Cl.
  *C12N 5/073* (2010.01)
  *C12M 1/33* (2006.01)
  *C12M 1/00* (2006.01)

(52) U.S. Cl.
  CPC ............. *C12N 5/0605* (2013.01); *C12M 45/02* (2013.01); *C12M 45/09* (2013.01)
  USPC .......................................................... 241/69

(58) Field of Classification Search
  CPC ...................................................... B02C 18/10
  USPC ......................................... 435/306.1; 422/513
  See application file for complete search history.

(56) References Cited

U.S. PATENT DOCUMENTS

| | | | |
|---|---|---|---|
| 3,380,499 A | 4/1968 | Vocci et al. | |
| 3,666,187 A | 5/1972 | Norris | |

(Continued)

FOREIGN PATENT DOCUMENTS

| | | |
|---|---|---|
| EP | 1228806 A1 | 8/2002 |
| EP | 1385609 A1 | 2/2004 |

(Continued)

OTHER PUBLICATIONS

International Search Report and Written Opinion for PCT/US2012/064130, mailed Jan. 25, 2013, 16 pages.

(Continued)

*Primary Examiner* — Sally Merkling
(74) *Attorney, Agent, or Firm* — Goodwin Procter LLP

(57) ABSTRACT

The present invention efficiently and cost-effectively extracts and collects cells from a tissue. The inventors have discovered that the tissue can be effectively fragmented and the resulting cells can be purified using a system or kit with multiple components. An advantage of the present invention is that tissue processing takes place in a closed system such that sterility can be maintained throughout the process, even if certain components are removed during processing, for example through the use of valves, clamps, and heat seals. Furthermore, any or all of the steps can be automated or manually accomplished, according to the specific needs of the application or the user.

30 Claims, 17 Drawing Sheets

(56) References Cited

U.S. PATENT DOCUMENTS

| | | |
|---|---|---|
| 4,151,959 A | 5/1979 | Deister |
| 4,307,846 A | 12/1981 | Spelsberg |
| 4,509,695 A | 4/1985 | Bessman |
| 4,828,395 A | 5/1989 | Saito et al. |
| 5,731,199 A | 3/1998 | Roggero et al. |
| 6,120,474 A | 9/2000 | Okuda et al. |
| 6,817,750 B1 | 11/2004 | Sands |
| 6,863,431 B2 | 3/2005 | Yacko et al. |
| 6,890,728 B2 | 5/2005 | Dolecek et al. |
| 7,052,172 B2 | 5/2006 | Jahn et al. |
| 7,060,494 B2 | 6/2006 | Bhat |
| 7,172,334 B2 | 2/2007 | Chiappetta |
| 7,270,284 B2 | 9/2007 | Liao et al. |
| 7,306,741 B2 | 12/2007 | Dolecek et al. |
| 7,611,473 B2 | 11/2009 | Boock et al. |
| 7,897,388 B2 | 3/2011 | Shetty et al. |
| 8,034,003 B2 | 10/2011 | Pesce et al. |
| 8,048,952 B2 | 11/2011 | Wynne et al. |
| 8,119,121 B2 | 2/2012 | Fraser et al. |
| 8,278,102 B2 | 10/2012 | Ennis et al. |
| 8,367,409 B2 | 2/2013 | Abbot et al. |
| 2002/0197631 A1 | 12/2002 | Lawrence et al. |
| 2003/0054331 A1 | 3/2003 | Fraser et al. |
| 2003/0161818 A1 | 8/2003 | Weiss et al. |
| 2004/0193071 A1 | 9/2004 | Binette et al. |
| 2004/0197367 A1 | 10/2004 | Rezania et al. |
| 2005/0139704 A1 | 6/2005 | Liao et al. |
| 2005/0148074 A1 | 7/2005 | Davies et al. |
| 2006/0192038 A1 | 8/2006 | Sekine |
| 2007/0082389 A1 | 4/2007 | Clark et al. |
| 2007/0259330 A1 | 11/2007 | Goddard et al. |
| 2008/0069895 A1 | 3/2008 | Liu et al. |
| 2008/0118477 A1 | 5/2008 | Christopherson |
| 2008/0132803 A1 | 6/2008 | Friedlander |
| 2008/0152630 A1 | 6/2008 | Ginis et al. |
| 2008/0196602 A1 | 8/2008 | Sands |
| 2008/0274087 A1 | 11/2008 | Li et al. |
| 2008/0305148 A1 | 12/2008 | Fu |
| 2009/0022696 A1 | 1/2009 | Bernstein et al. |
| 2009/0068153 A1 | 3/2009 | Vitelli et al. |
| 2009/0074731 A1 | 3/2009 | Librach et al. |
| 2009/0081171 A1 | 3/2009 | Fu et al. |
| 2009/0124007 A1 | 5/2009 | Cho |
| 2009/0136988 A1 | 5/2009 | Reschiglian et al. |
| 2009/0142835 A1 | 6/2009 | Kobayashi et al. |
| 2009/0170059 A1 | 7/2009 | Klingemann |
| 2009/0232781 A1 | 9/2009 | Fu |
| 2009/0232782 A1 | 9/2009 | Fu |
| 2009/0280093 A1 | 11/2009 | Friedlander |
| 2009/0291061 A1 | 11/2009 | Riordan et al. |
| 2010/0034783 A1 | 2/2010 | Son et al. |
| 2010/0098675 A1 | 4/2010 | Tankovich |
| 2010/0104539 A1 | 4/2010 | Daniel et al. |
| 2010/0247495 A1 | 9/2010 | Ichim et al. |
| 2011/0002883 A1 | 1/2011 | Petrikovsky et al. |
| 2011/0151556 A1 | 6/2011 | Kallis et al. |
| 2011/0158969 A1 | 6/2011 | Chopp |
| 2011/0189254 A1 | 8/2011 | Liu et al. |
| 2011/0256186 A1 | 10/2011 | Font Perez et al. |
| 2011/0274664 A1 | 11/2011 | Harn et al. |
| 2011/0293667 A1 | 12/2011 | Baksh et al. |
| 2011/0312091 A1 | 12/2011 | Zhao et al. |
| 2012/0093783 A1 | 4/2012 | Pinkernell et al. |
| 2012/0141595 A1 | 6/2012 | Tseng et al. |
| 2012/0171762 A1 | 7/2012 | Coelho et al. |
| 2012/0189583 A1 | 7/2012 | Liu et al. |
| 2012/0214659 A1 | 8/2012 | Do et al. |
| 2012/0258459 A1 | 10/2012 | Huang |
| 2012/0270314 A1 | 10/2012 | Ding et al. |
| 2012/0276215 A1 | 11/2012 | Riordan et al. |
| 2012/0276518 A1 | 11/2012 | Gillis |
| 2012/0294909 A1 | 11/2012 | Daniel et al. |
| 2012/0315259 A1 | 12/2012 | Friedlander |
| 2013/0034524 A1 | 2/2013 | Agha-Mohammadi |
| 2013/0059286 A1 | 3/2013 | Chang et al. |
| 2013/0059383 A1 | 3/2013 | Dijkhuizen Borgart et al. |

FOREIGN PATENT DOCUMENTS

| | | |
|---|---|---|
| GB | 1152418 A | 5/1969 |
| JP | 6143981 | 3/1986 |
| JP | 6143982 | 3/1986 |
| WO | WO-03086598 A1 | 10/2003 |
| WO | WO-2005/030936 A1 | 4/2005 |

OTHER PUBLICATIONS

Fossum et al. "Minced Skin for Tissue Engineering of Epithelialized Subcutaneous Tunnels" Tissue Eng Part A. Aug. 2009; 15(8): 2085-2092.

Castaneda, "Laboratory Diagnosis of Brucellosis in Man" Bull. Org. Mond. Bull. Wld. Hth Org. Sante, 1961, 24, 73-84.

D'Allessandris et al. "Autoclavable Dispensing Device" Air Force Aerospace Medical Research Laboratory, Feb. 1980, 8 pages.

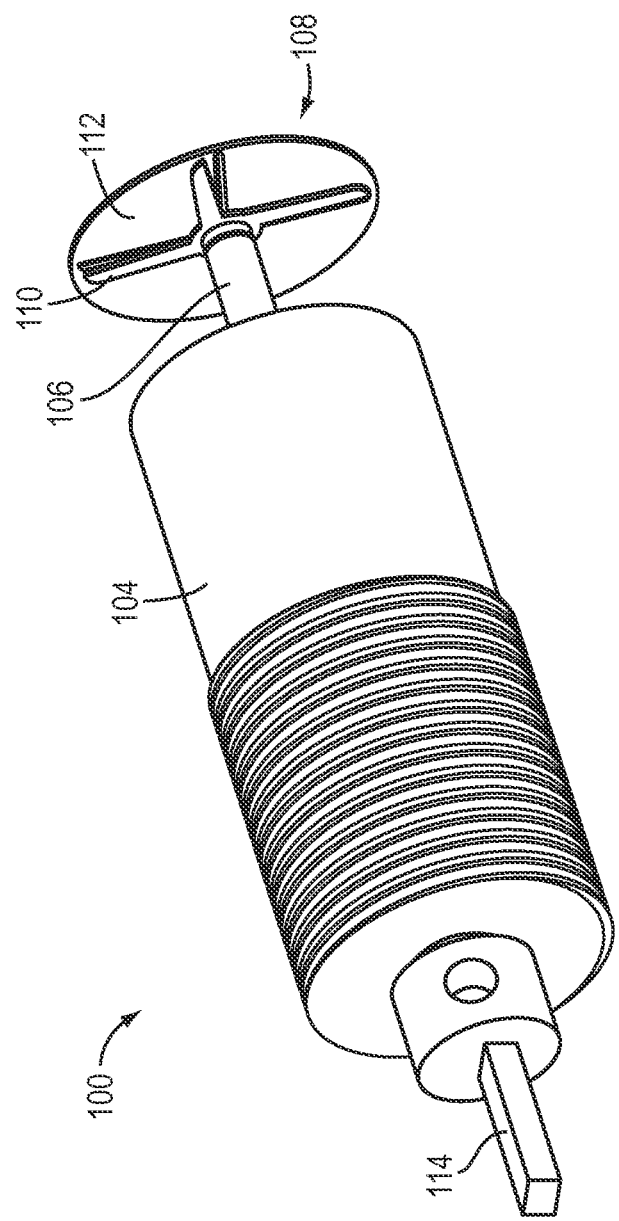

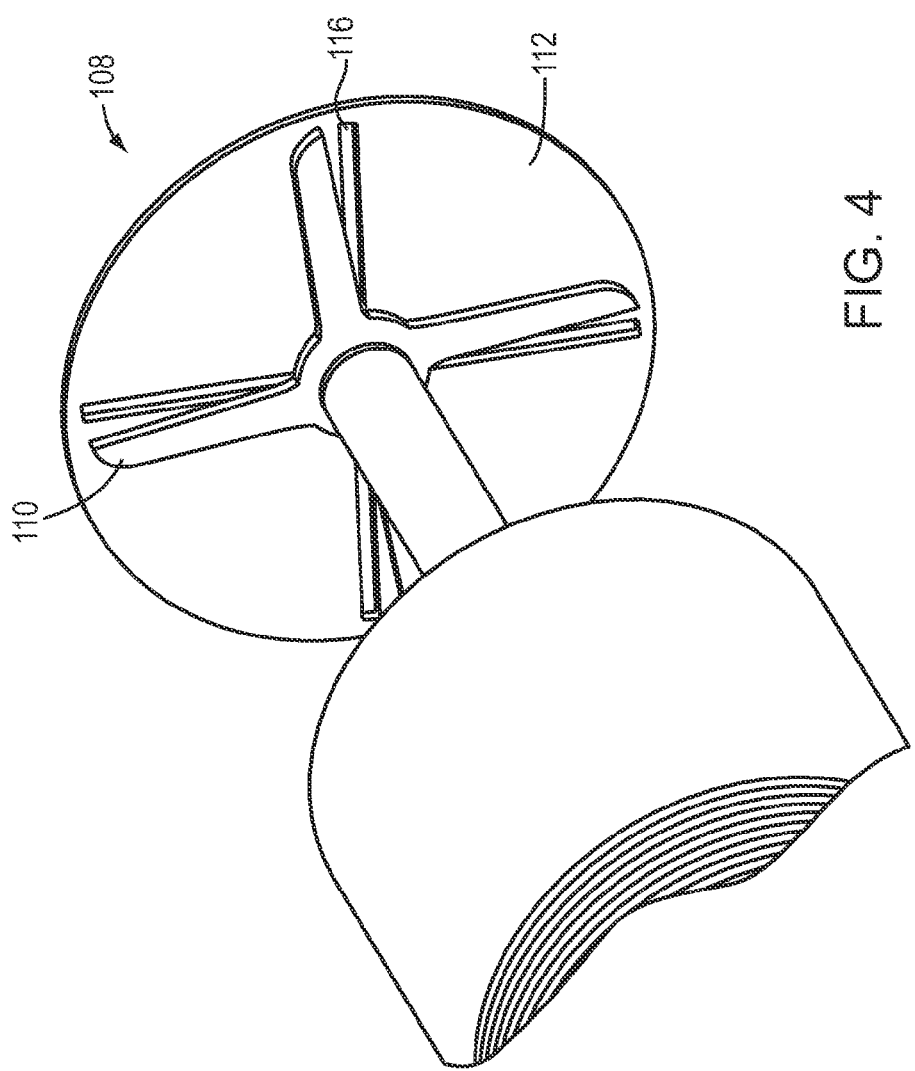

* CENTRIFUGATION NOT NECESSARY, OPTIONAL.

* CENTRIFUGATION NOT NECESSARY, OPTIONAL.

SYSTEMS AND METHODS FOR PROCESSING CELLS

CROSS-REFERENCE TO RELATED APPLICATIONS

This application is a continuation of, claims priority to and the benefit of, and incorporates herein by reference in its entirety U.S. patent application Ser. No. 13/933,034, which was filed on Jul. 1, 2013 and issued on Nov. 25, 2014 as U.S. Pat. No. 8,893,995. U.S. patent application Ser. No. 13/933,034 is a continuation of International Patent Application No. PCT/US2012/064130, which was filed on Nov. 8, 2012 and which itself claims priority to and the benefit of U.S. Provisional Patent Application No. 61/557,127, which was filed on Nov. 8, 2011. The contents of International Patent Application No. PCT/US2012/064130 and U.S. Provisional Patent Application No. 61/557,127 are also incorporated herein by reference in their entirety.

TECHNICAL FIELD

In various embodiments, the present invention relates to systems and methods for processing tissue to isolate and collect target cells.

BACKGROUND OF THE INVENTION

Purification of viable cells from a tissue sample can be a laborious process that involves dissection and other manual manipulation and processing steps, as well as, in some cases, cell culturing. Maintaining sterility of the cells during the purification process is also an important concern. Although laminar hoods can be used to maintain sterility, they suffer a number of disadvantages. For example, such hoods are expensive, relatively immobile, cumbersome to work with, and consume valuable laboratory space. Efficiency of the cell purification process is another concern that further complicates the purification process. Isolating rare cells, such as stem cells, from a tissue sample requires an efficient process to recover as many of the cells as possible.

There remains a need for a practical, cost-effective, sterile, and efficient mechanism and method for extracting and collecting cells, such as stem cells, for advancing potential therapies that rely on the administration of these cells.

SUMMARY OF THE INVENTION

The present invention efficiently and cost-effectively extracts and collects cells from a tissue. The inventors have discovered that the tissue can be effectively fragmented and the resulting cells can be purified using a system or kit with multiple components. An advantage of the present invention is that tissue processing takes place in a closed system such that sterility can be maintained throughout the process, even if certain components are removed during processing, for example through the use of valves, clamps, and heat seals. Furthermore, any or all of the steps can be automated or manually accomplished, according to the specific needs of the application or the user.

Thus, in one aspect, the invention relates to a tissue mincing tool. The tissue mincing tool includes a compartment for a tissue sample, a cutting surface at one end of the compartment, and a sterile, sealed container. The cutting surface separates the compartment from the sterile, sealed container, such that a tissue sample that passes through the cutting surface can be deposited within the container. The cutting surface can be dimensioned to mince the tissue sample into fragments having an average cross-section no greater than four square millimeters. For example, the number of square millimeters may be no greater than 3, 2, 1, 0.5, 0.3, 0.2, 0.1, or 0.05 in various embodiments of the invention. The tissue mincing tool can also include a second cutting surface for further reducing the average cross-section of the fragments. The cutting surface of the tissue mincing tool can include an automated cutting system. For example, the cutting surface may include semi-automatic scissors. One or more mincer screens may be positioned in proximity to the cutting surface. The tissue mincing tool may further include a suction cup for stabilizing the tool during operation thereof. The tissue mincing tool also or alternatively can include a fluid conduit in communication with the sterile, sealed container, and a separator unit such as one or more filters within the fluid conduit. The sterile, sealed container optionally includes at least one sealed access port permitting the sterile introduction of a fluid into the container.

In the tissue mincing tool, the compartment for the tissue sample can incorporate one or more features to facilitate the application of a force to the tissue sample, impelling it beyond the cutting surface and into the sterile, sealed container. For example, a portion of the compartment can be shaped to receive a solid member to press the tissue sample. Such a solid member can optionally be included with the tissue mincing tool, whether connected to it or provided as a separate component.

In one embodiment, a portion of the compartment near the cutting surface has a substantially constant cross-section, such that a comparably shaped solid member may be introduced into the compartment and fill that portion, while pressing the tissue sample into or through the cutting surface. In another embodiment, the compartment near the cutting surface has a tapered or cone-shaped end. In some embodiments, an interior surface of the compartment is threaded, such that a threaded solid member may be guided into the compartment. In some embodiments, the compartment also includes a gasket, which can provide an improved seal when a solid member is introduced into the compartment. In yet another embodiment, the tissue mincing tool includes a shaft crank for moving the cutting surface towards the tissue sample.

The invention also provides methods of using any of the above-described tissue mincing tools by impelling the tissue sample through the cutting surface of the tool. The invention provides methods of mincing a tissue sample and optionally injecting an enzyme into the sterile, sealed container, such that the enzyme enhances the digestion of the minced tissue. The enzyme can be a protease, such as collagenase, hyaluronidase, or dispase, separately or in combination. These steps can optionally be incorporated into a method of separating cells from the tissue sample by mincing and/or digesting the tissue sample and removing fragments larger than about 40 microns (e.g. fragments retained by a filter having a pore size of about 500 microns, or fragments retained by a filter having a pore size of about 300 microns, or fragments retained by a filter having a pore size of about 250 microns, or fragments retained by a filter having a pore size of about 150 microns, or fragments retained by a filter having a pore size of about 100 microns, or fragments retained by a filter having a pore size of about 70 microns, or fragments retained by a filter having a pore size of about 40 microns). These larger fragments, referred to herein as "undigested tissue," can be removed by filtering or sedimentation. These methods are effective for purifying cells from any of a variety of solid tissues. For example, the methods described herein can separate cells, such as stem cells, from fat tissue or afterbirth tissue, such as placental or umbilical cord tissue or, more specifically, a tissue comprising Wharton's Jelly. In some embodiments, the tissue sample is substantially free of blood vessels, which can optionally be dissected from a tissue before the tissue is placed in the compartment.

In another aspect, the invention relates to a cell collection method including sedimenting cells in a cell collection device. The cell collection device includes a sterile container for a fluid including cells and a fluid passageway in communication with the sterile container. The fluid passageway includes a cell capture zone, such that the volume of the cell capture zone can be less than 5% of the volume of the sterile container and the sterile container and the cell capture zone can be configured such that sedimentation of the cells from the fluid in the sterile container concentrates the cells in the cell capture zone. This aspect or any of the following aspects can have any of the following embodiments. The cell collection device further includes a second sterile container in communication with the fluid passageway and/or a removable clamp to regulate passage of material into the second sterile container. The second sterile container can be heat-sealable and/or a bag. The cell collection method can also include centrifuging the cell collection device to accelerate sedimentation of the cells, and the cells can be Wharton's Jelly stem cells. The fluid includes mechanically minced and/or enzymatically digested umbilical cord tissue. The cell collection method can further include adding a cryoprotectant to the cells; the cryoprotectant includes DMSO, albumin, and/or dextran. The method can also include adding autologous plasma to the cells.

In still another aspect, the invention relates to a cell collection device having a fluid including cells, a sterile container for housing the cells, and a fluid passageway in communication with the sterile container. The fluid passageway includes a cell capture zone, wherein the volume of the cell capture zone can be less than 5% of the volume of the sterile container and the sterile container and the cell capture zone can be configured such that sedimentation of the cells from the fluid in the sterile container concentrates the cells in the cell capture zone. This aspect or any of the following aspects can have any of the following embodiments. The cell collection device also or alternatively includes a second sterile container in communication with the fluid passageway and/or a removable clamp to regulate passage of material into the second sterile container. The second sterile container can be heat-sealable and/or a bag.

In yet another aspect, the invention relates to a cell collection device having a sterile container for a fluid comprising cells, such that the sterile container can be adapted for use in sedimentation, and a fluid passageway in communication with the sterile container. The fluid passageway includes first and second valves defining a cell capture zone therebetween, such that the volume of the cell capture zone can be less than 5% of the volume of the sterile container and the sterile container and the cell capture zone can be configured such that sedimentation of the cells from the fluid in the sterile container concentrates the cells in the cell capture zone. This aspect or any of the following aspects can have any of the following embodiments. The sterile container can be adapted for use in centrifugation. The cell collection device also or alternatively includes a second sterile container in communication with the second valve and/or a removable clamp to regulate passage of material into the second sterile container. The second sterile container can be heat-sealable and/or a bag.

In still yet another aspect, the invention relates to a cell collection device having a sterile container for housing the cells, a fluid passageway in communication with the sterile container, and a second sterile container in communication with the fluid passageway. The fluid passageway includes a cell capture zone, such that the volume of the cell capture zone is less than 5% of the volume of the sterile container and the sterile container and the cell capture zone can be configured such that sedimentation of the cells from the fluid in the sterile container concentrates the cells in the cell capture zone. The second sterile container includes an element selected from the group consisting of a bag, a heat-sealable container, and a removable clamp.

In another aspect, the invention relates to cell collection device that includes a compartment for receiving a tissue; a cutting surface dimensioned to mince the tissue sample into fragments having an average cross-section no greater than four square millimeters; a sterile, sealed container for holding a suspension of the minced tissue, the sterile container having a volume at least ten times greater than the volume of the compartment for receiving a tissue; a filter bag in fluid communication with the sterile, sealed container; and a sedimentation bag in fluid communication with the filter bag. The filter bag contains at least one filter having a pore size sufficiently small to retain particles larger than about 250 μm. The sedimentation bag includes a tapered portion to promote the concentration of sedimented cells.

BRIEF DESCRIPTION OF THE FIGURES

Other features and advantages of the present invention, as well as the invention itself, can be more fully understood from the following description of the various embodiments, when read together with the accompanying drawings, in which:

FIG. 3 is a schematic perspective view of the solid member of FIG. 2;

FIG. 4. is a schematic perspective view partially showing a cutting surface, according to an embodiment of the invention;

DETAILED DESCRIPTION

To provide an overall understanding of the invention, certain illustrative embodiments will now be described, including systems and methods for processing cells. However, it will be understood by one of ordinary skill in the art that the systems and methods described herein may be adapted and modified as is appropriate for the application being addressed and that the systems and methods described herein may be employed in other suitable applications. All such adaptations and modifications are to be considered within the scope of the invention. Furthermore, it is to be understood that the features of the various embodiments described herein are not mutually exclusive and can exist in various combinations and permutations.

Tissue Mincing Tool

Figure 1:
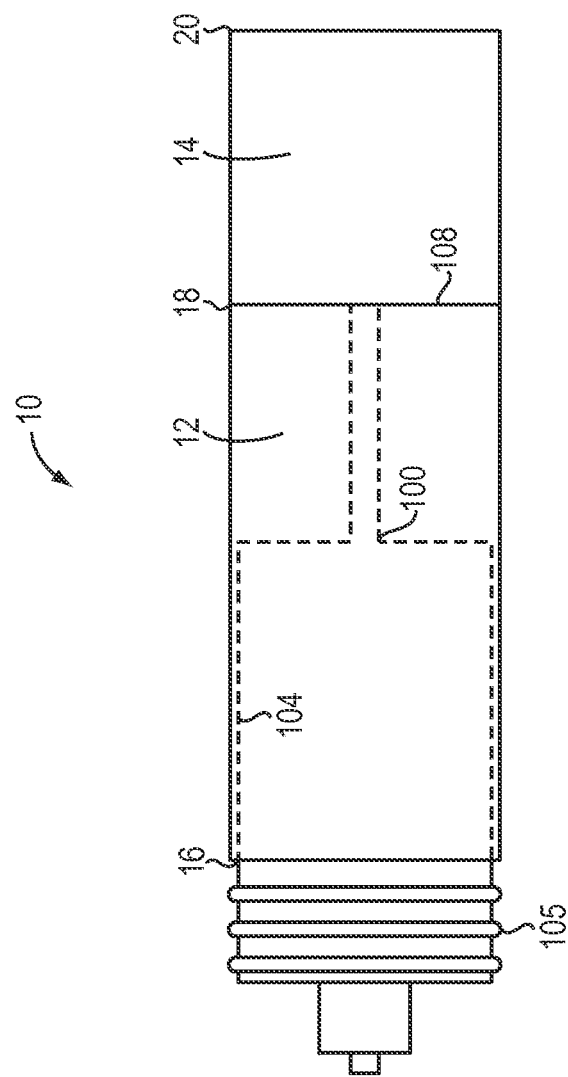
FIG. 1 schematically depicts a tissue mincing tool, according to an embodiment of the invention.

FIG. 1 schematically depicts a tissue mincing tool 10 according to one embodiment of the invention. The tissue mincing tool 10 includes a compartment 12 within which a tissue sample can be received and be initially housed, and a sterile, sealed container 14. The compartment 12 extends between first and second ends 16, 18, while the sterile, sealed container 14 itself extends between first and second ends 18, 20. A cutting surface 108 is located at the second end 18 of the compartment 12 or, equivalently, at the first end 18 of the sterile, sealed container 14, and therefore separates the compartment 12 from the sterile, sealed container 14. As illustrated, the tissue mincing tool 10 also includes a solid member 100. The solid member 100 is depicted to be partially located within (as shown in phantom) the compartment 12. A part of the solid member 100 is also shown to be located outside the compartment 12. Threads 105 are depicted on that exterior part of the solid member 100.

Figure 2:
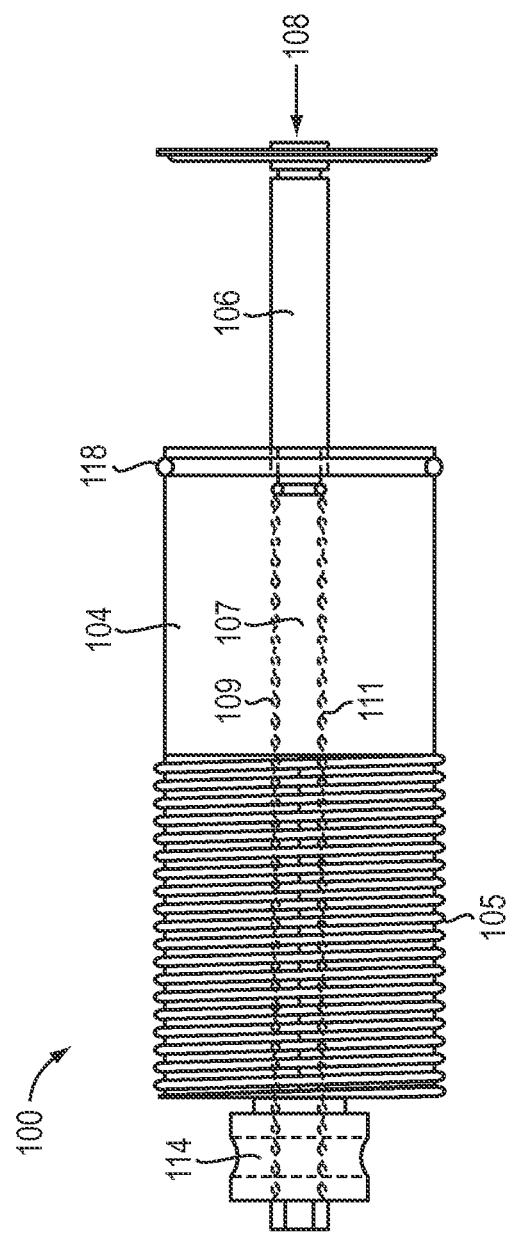
FIG. 2 is a schematic perspective view of a solid member of a tissue mincing tool, according to an embodiment of the invention.

FIG. 2 depicts an embodiment of the solid member 100 of the tissue mincing tool 10. Other portions of the tissue mincing tool 10 (e.g., the compartment 12 and the sterile, sealed container 14) are not shown. The solid member 100 includes a larger diameter plunger 104 (shown with the threads 105) and a smaller diameter screw shaft 106. A handle 114 is disposed at one end of the solid member 100. At the opposite end of the solid member 100, the cutting surface 108 is attached to the end of the smaller diameter screw shaft 106. As illustrated, the smaller diameter screw shaft 106 extends from the cutting surface 108 to the handle 114 (to which the smaller diameter screw shaft 106 is also coupled) and, in so doing, the smaller diameter screw shaft 106 runs through a hollow (e.g., central) portion 107 of the larger diameter plunger 104. In one embodiment, the screw shaft 106 features threads 109 along a certain length thereof and the plunger 104 includes complementary grooves 111 within its hollow portion 107. In this way, the plunger 104 is threadably engaged with the screw shaft 106. Accordingly, when the handle 114 is rotated, the screw shaft 106 is also caused to rotate, as is (optionally) the cutting surface 108 that is attached to the end of the screw shaft 106. Moreover, rotation of the screw shaft 106 causes translation of the plunger 104, for example towards the cutting surface 108. A tissue sample housed within the compartment 12 between the plunger 104 and the cutting surface 108 may thus be pressed into contact with the (optionally rotating) cutting surface 108 and, as described further below, cut thereby.

The threaded portion 105 of the larger diameter plunger 104 can engage and mate with a complementary threaded interior portion of the compartment 12 that receives the tissue sample. Threaded engagement between the plunger 104 and the compartment 12 provides for leverage and control so that a user can more easily translate the plunger 104 within the compartment 12 using the handle 114, as well as slide or push the tissue sample towards and through the cutting surface 108. As illustrated in FIG. 1, the plunger 104 is sized to mate with and substantially fill an interior hollow cavity of the compartment 12. In an embodiment, with reference again to FIG. 2, a gasket 118 may be disposed at one end of the plunger 104. Together, the gasket 118 and plunger 104 may substantially fill an inner diameter of the interior hollow cavity of the compartment 12, thereby creating an air-tight, vacuum seal in the compartment 12. Gasket 118 may be substantially complementary in shape to cutting surface 108. For example, the bottom surface of the gasket and the top surface of the cutting surface 108 can both be round or flat. In an embodiment, gasket 118 forms a flat surface. A tissue sample is impelled through cutting surface 108 and, thus, minced when gasket 118 contacts and drives the tissue sample.

The cutting surface 108 can be any surface configured to cut, parse, or separate a tissue sample into smaller portions without damaging the cells from the tissue sample when the tissue sample is pushed through the cutting surface 108. For example, the cutting surface 108 can mince a tissue sample into smaller portions with an average cross-section no greater than four square millimeters, or one square millimeter, though cutting surfaces that can mince the tissue sample into larger or smaller portions are contemplated. A tissue mincing tool can include a second cutting surface to further reduce the average cross-section of the minced tissue samples. Examples of a cutting surface include a grate with sharp edges, multiple sharp wires across an opening, a steel plate or disc with multiple holes resting on a lip inside a compartment, holes in a plate that are offset and have a sharp edge, and a mesh of sharp surfaces defining apertures. Additionally or alternatively, in an embodiment in which a cutting surface defines apertures, an end of the plunger 104 can form multiple projections, such as fingers, that mate with the apertures of the cutting surface 108 to assist in pushing the tissue sample through the cutting surface 108. In an alternative embodiment, the end of the plunger 104 can be flat. Moreover, the cutting surface 108 can be textured or can form multiple projections (e.g., a cleat) to create a frictional surface or to keep the tissue sample on the cutting surface 108 as pressure is applied to the tissue sample. In a further embodiment, the cutting surface 108 may include an automated cutting system, such as a semi-automatic scissors.

In an embodiment, an optional nose nut (not shown) may be disposed about the cutting surface 108 to retain the cutting surface 108 in position as a tissue sample is being impelled therethrough. For example, the optional nose nut can be removably attached to the compartment 12 that receives the tissue sample. The optional nose nut can include a projection that engages with a recessed surface of the compartment 12 to form a snap-fit connection. Additionally or alternatively, a threaded portion of the optional nose nut can engage a similarly and complementary threaded portion of the compartment 12. When the optional nose nut is fully engaged with the compartment 12, the cutting surface 108 is disposed on and retained in position by a lip of the optional nose nut.

FIG. 3 depicts a perspective view of the solid member 100 of the tissue mincing tool 10. Other portions of the tissue mincing tool (e.g., the compartment 12 and the sterile, sealed container 14) are not shown. As before, the solid member 100 includes a larger diameter plunger 104 (shown with the threads 105) and a smaller diameter screw shaft 106. The handle 114 is disposed at one end of the solid member 100. At the opposite end of the solid member 100, the cutting surface 108 is attached to the end of the smaller diameter screw shaft 106. In one embodiment, as illustrated, the cutting surface 108 includes a cutting blade 110 adjacent a mincing disc 112.

FIG. 4 depicts a perspective view of an exemplary cutting surface 108 of the tissue mincing tool 10. The cutting surface 108 includes the cutting blade 110. Additionally, the cutting surface 108 includes the mincing disc 112 with apertures 116 that allow tissues samples to be impelled therethrough.

Figure 5B:
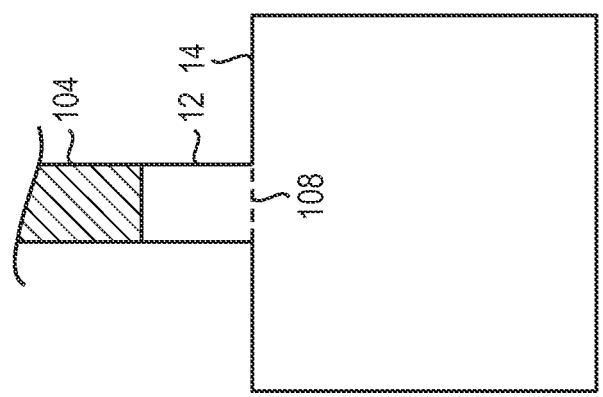
FIGS. 5A and 5B are schematic views partially showing a solid member and its complementary compartment, according to embodiments of the invention.
Figure 5A:
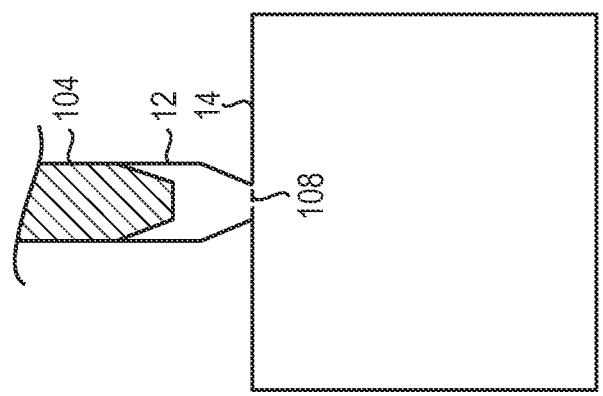

FIGS. 5A and 5B depict two embodiments of a solid member 100 of a tissue mincing tool 10. In one embodiment depicted in FIG. 5A, the plunger 104 of the solid member 100 is substantially cylindrical in shape near its end. In a second embodiment depicted in FIG. 5B, the plunger 104 of the solid member 100 has a tapered or cone-shaped end. In each embodiment, the solid member 100 is shaped to mate with and to fill the compartment 12 that is complementarily shaped, such that the solid member 100 is movable within the compartment 12 to impel a tissue sample disposed within the compartment 12 through the cutting surface 108. As the tissue sample passes through the cutting surface 108, the cut portions thereof are deposited within the sterile, sealed container 14, which may be, for example, a bag. Additionally or alternatively, the interior cavity of the compartment 12 can define a recessed channel or surface (e.g., a cam surface) to engage a projection protruding from the plunger 104 such that solid member 100 can be removably secured to the compartment 12 and the user still has leverage and control to translate the solid member 100 into the compartment 12 (not shown).

Figure 6B:
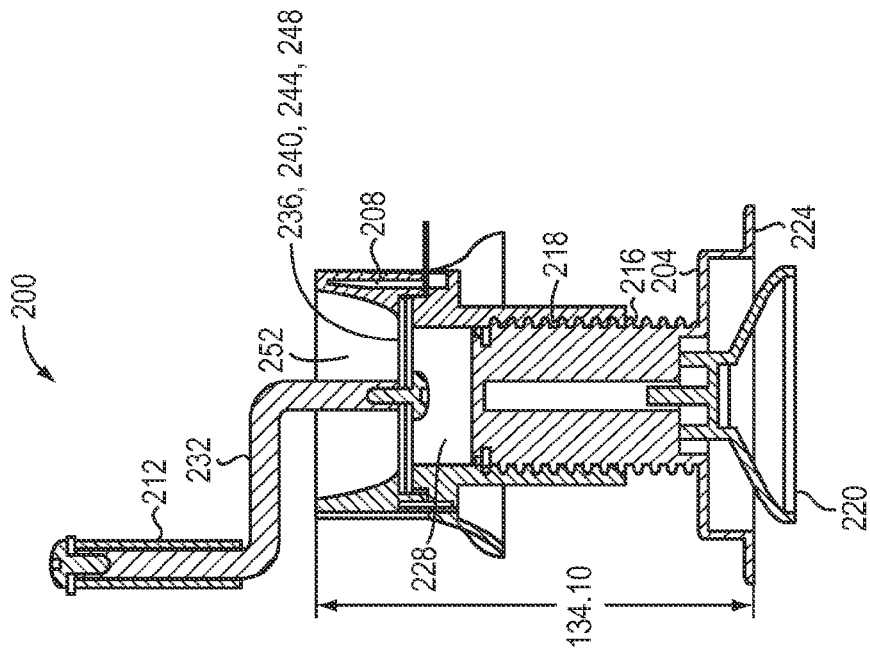
FIG. 6B is a cross-sectional view along the line E-E of the tissue mincing tool of FIG. 6A.
Figure 6A:
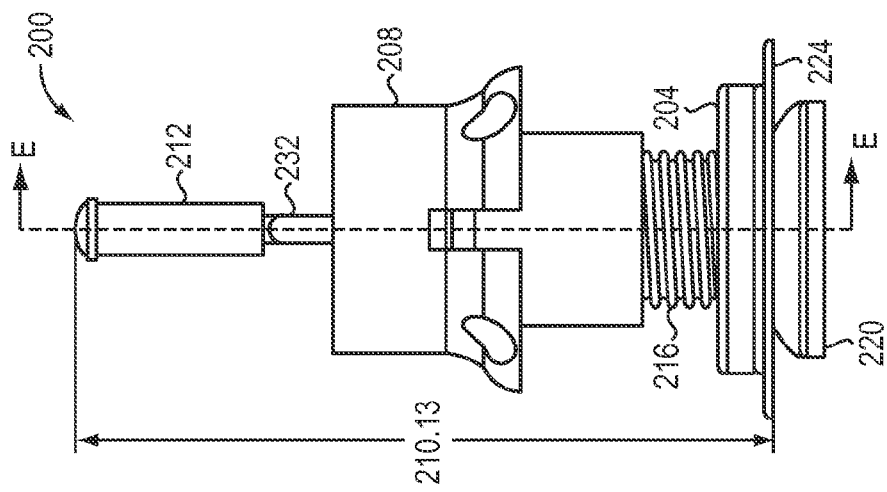
FIG. 6A is a side view of a tissue mincing tool, according to another embodiment of the invention.
Figure 6C:
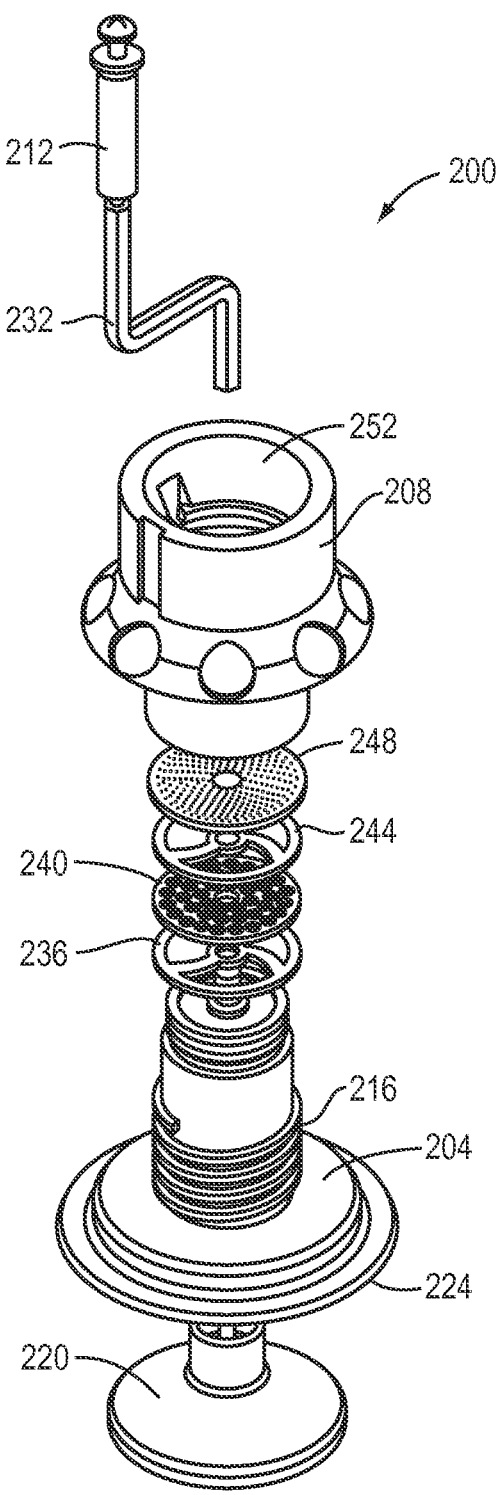
FIG. 6C is an exploded view of the tissue mincing tool of FIG. 6A.

FIG. 6A depicts a side view of a tissue mincing tool 200 according to another embodiment of the invention. FIG. 6B depicts a cross-sectional view along the line E-E of the tissue mincing tool 200 shown in FIG. 6A, while FIG. 6C depicts an exploded view of the tissue mincing tool 200 shown in FIG. 6A. The tissue mincing tool 200 includes a base 204, a reservoir 208, and a handle 212. As shown, the base 204 may include a threaded portion 216 for threadably engaging the reservoir 208. For example, an interior surface of the reservoir 208 may feature grooves 218 that complement the threaded portion 216 of the base 204. Thus, during assembly of the tissue mincing tool 200, the reservoir 208 may be screwed onto the base 204.

As illustrated, a suction cup 220 may be coupled to a bottom portion 224 of the base 204. In one embodiment, the suction cup 220 provides stability for the tissue mincing tool 200. For example, in operation, a user may couple the tissue mincing tool 200 to a table (or other support surface) using the suction cup 220. Stability is thereby provided to the tissue mincing tool 200 when, for example, the user turns the handle 212 as further described below, or otherwise imparts force to the tissue mincing tool 200.

As most clearly shown in FIG. 6B, included within the reservoir 208 is a compartment 228 for initially housing a tissue sample. In addition, at least one cutting surface (which is coupled to the handle 212 through a shaft crack 232) is moveable within the reservoir 208. For example, as most clearly shown in FIG. 6C, a first cutting surface 236, a first mincer screen 240, a second cutting surface 244, and a second mincer screen 248 (each of which are coupled to the handle 212 through the shaft crank 232) may be moveable within the reservoir 208 through actuation (e.g., rotation) of the shaft crank 232. The shaft crank 232 may, for example, be manually actuated by a user via the handle 212, or, alternatively, may be automatically machine-actuated via a separate device. As will be understood by one of ordinary skill in the art, the first and second cutting surfaces 236, 244 may be any of the exemplary cutting surfaces described above. In addition, the first and second mincer screens 240, 248 may, as illustrated, include differently-sized apertures.

In operation, as the shaft crank 232 is rotated, the first and second cutting surfaces 236, 244 are likewise rotated and move downward within the reservoir 208 toward the tissue sample that is housed within the compartment 228. The first cutting surface 236 makes contact with and cuts the tissue sample into one or more smaller portions. Those smaller tissue portions are then passed through the apertures of the first mincer screen 240, are again cut into even smaller portions by the second cutting surface 244, and are finally passed through the apertures of the second mincer screen 248. The first and second cutting surfaces 236, 244 are rotated and moved downwards within the reservoir 208 until substantially all of the tissue sample (or at least a sufficient amount of the tissue sample for a given application) is minced and passes through the second screen 248. Upon passing through the second screen 248, the minced tissue sample is collected and housed within a container 252 of the reservoir 208. Although not depicted as such in FIGS. 6A-6C, the top portion of the reservoir 208 may in fact be capped and the interior portion of the reservoir 208 sterilized, such that the container 252 is a sterile, sealed container 252.

As will be understood by one of ordinary skill in the art, and as described above, the compartment 228 of the reservoir 208 is, as shown in FIG. 6B, located below the first and second cutting surfaces 236, 244 and first and second mincer screens 240, 248, while the sterile, sealed container 252 of the reservoir 208 is located above the first and second cutting surfaces 236, 244 and first and second mincer screens 240, 248. As such, in the embodiment of the tissue mincing tool 200 depicted in FIGS. 6A-6C, the sizes of the compartment 228 and of the sterile, sealed container 252 vary as the first and second cutting surfaces 236, 244 are rotated downwards (or upwards).

As will also be understood by one of ordinary skill in the art, the depiction of the tissue mincing tool 200 in FIGS. 6A-6C is non-limiting. In fact, variations, modifications, and other implementations are contemplated. For example, fewer or more than two cutting surfaces 236, 244 and/or two mincer screens 240, 248 may be employed. As another example, the shaft crank 232 and handle 212 may be coupled such that the handle 212 is rotatable within a vertical plane rather than a horizontal plane (as illustrated).

Figure 7:
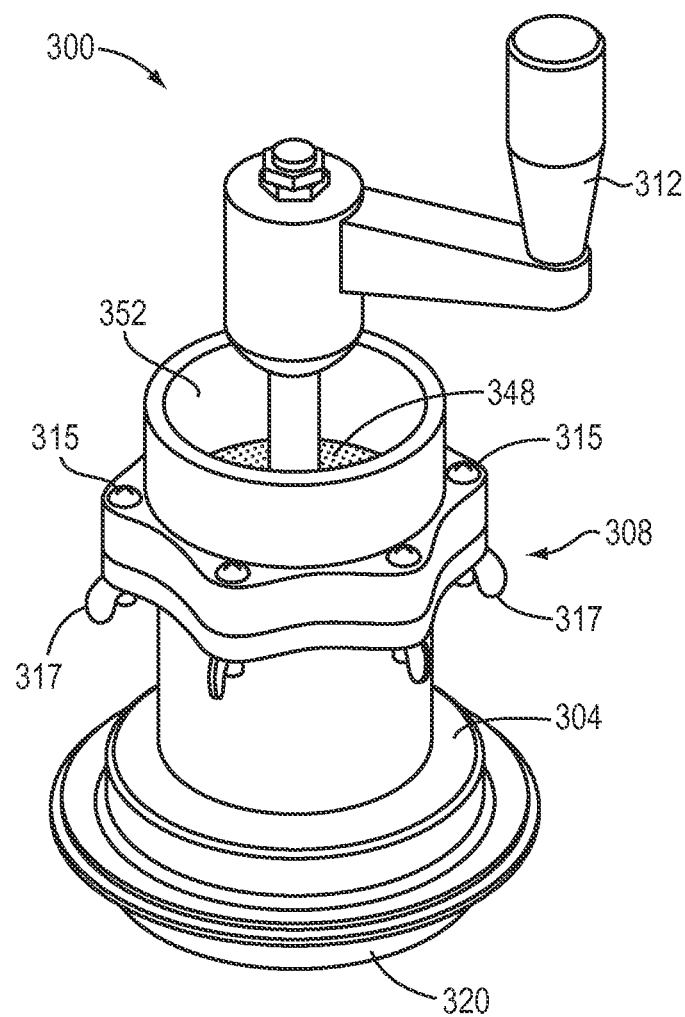
FIG. 7 is a schematic perspective view of a tissue mincing tool, according to yet another embodiment of the invention.

FIG. 7 depicts a tissue mincing tool 300, according to another view of an embodiment of the invention, whose principal of operation is similar to that of the tissue mincing tool 200 depicted in FIGS. 6A-6C. As before, the tissue mincing tool 300 includes a base 304, a reservoir 308, and a handle 312. As shown, a top portion of the reservoir 308 is coupled to a bottom portion thereof through the use of screws 315 and wing nuts 317. The tissue mincing tool 300 also includes a suction cup 320 to provide the aforedescribed stability to the tool 300 during operation. The container 352 of the reservoir 308 within which the minced tissue sample is collected after passing through, for example, a second screen 348 is also illustrated. As before, the top portion of the reservoir 308 may be capped and the interior portion of the reservoir 308 sterilized, such that the container 352 is a sterile, sealed container 352.

Cell Isolation and Collection Method

Figure 8:
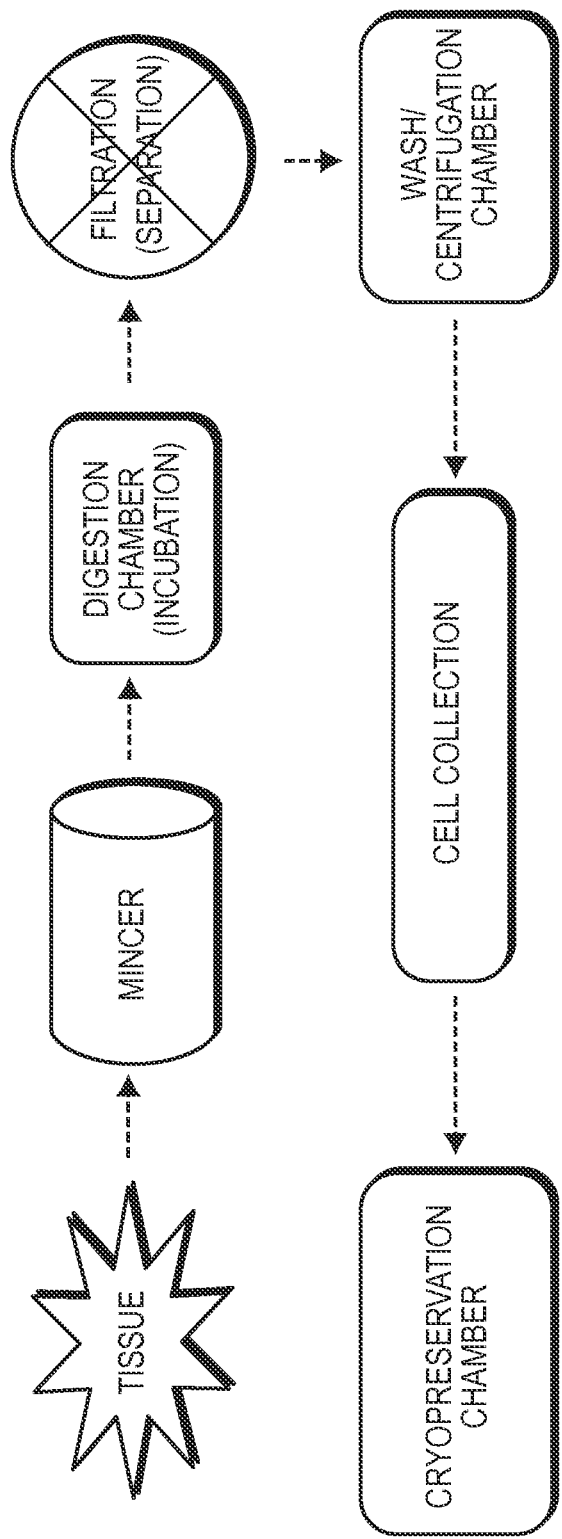
FIG. 8 provides an overview of the procedural steps for collecting and isolating desired cells from a tissue sample, according to an embodiment of the invention.

The invention also provides methods for efficient and sterile processing of tissue to isolate and to collect target cells. FIG. 8 provides an overview of the procedural steps for isolating and collecting cells. Generally, a tissue sample can be initially minced using any of the above-described tissue mincing tools by impelling the tissue sample through the cutting surface of the tool and into a sterile, sealed container. The invention also provides optional methods of further digesting the tissue sample by exposing it to a chemical or an enzyme. For example, the minced tissue may be digested by injecting an enzyme into the container, such that the enzyme digests the minced tissue. The enzyme can be a protease, such as collagenase, hyaluronidase, or dispase, separately or in combination. These steps are additionally or optionally incorporated into a method of separating minced and/or enzymatically digested tissue sample from any larger fragments ("undigested tissue," as described above), for example, decanting, aspiration, sedimentation, or preferably, filtering. In some embodiments, the minced and/or enzymatically digested tissue, which can be viscous, is washed or diluted before a separating step. The separation of the target cells from the minced and/or enzymatically digested tissue can be accomplished by sedimentation of the cells from a mixture containing the minced and/or enzymatically digested tissue. Although gravity sedimentation can be used, the sedimentation process can be accelerated by, for example, centrifugation. Additionally, and alternatively, the target cells are moved into a sterile container to be cryo-preserved for later use.

Figure 9:
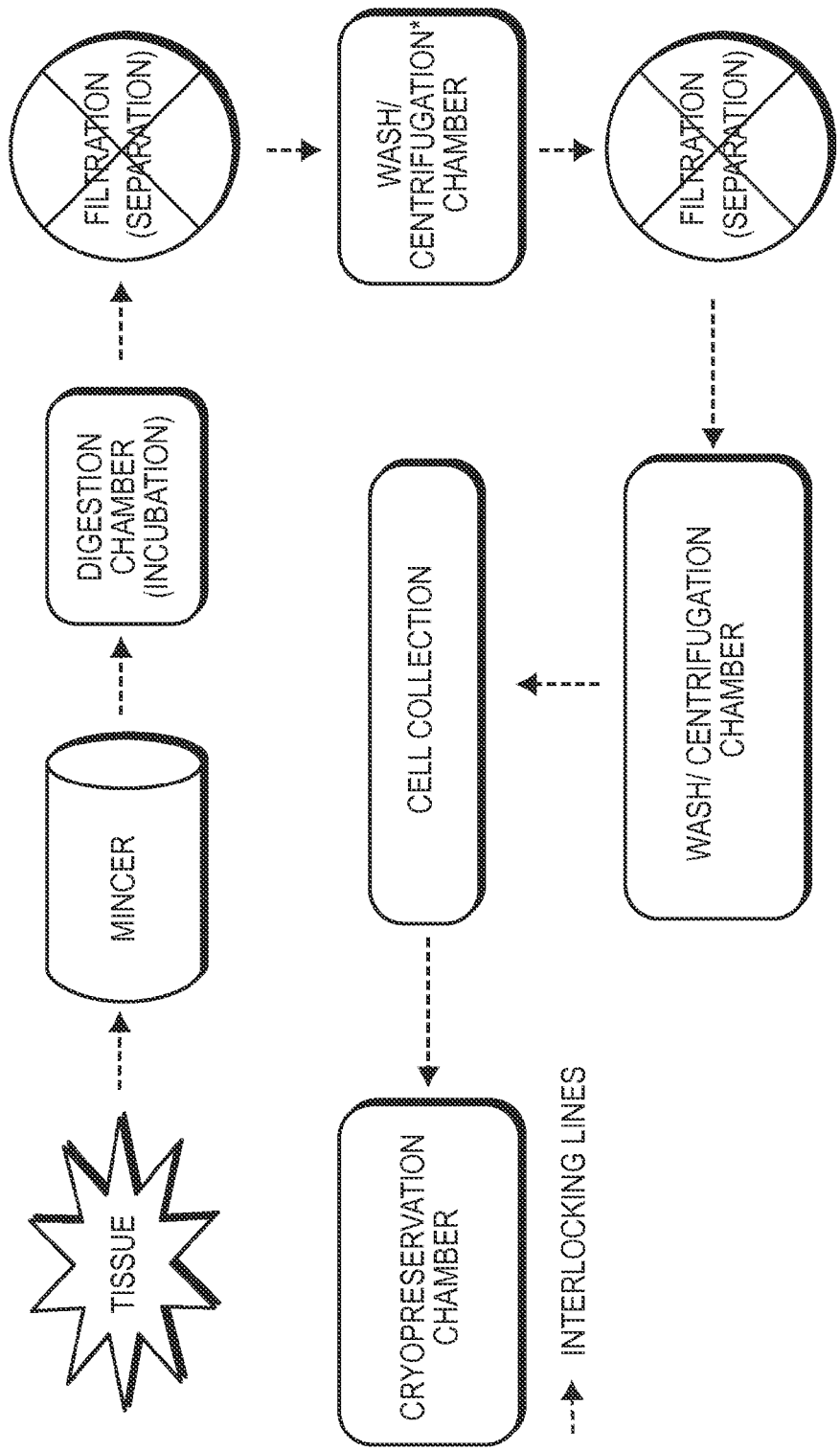
FIG. 9 provides an overview of the procedural steps for collecting and isolating desired cells from a tissue sample, according to an embodiment of the invention.

In an embodiment, methods for separating minced and/or enzymatically digested tissue sample from undigested tissue may include two or more filtration steps as depicted in FIG. 9. For example, minced and/or enzymatically digested tissue sample may be subjected to multiple filtration steps using filters of varying sizes. In an embodiment, the minced and/or enzymatically digested tissue sample is initially subjected to a first filtration step using a large-pore filter of, e.g., about 500 microns, about 250 microns, about 150 microns or about 100 microns, for removing coarse undigested tissue. Additionally, a second filtration step can be carried out to filter the eluate from the first filtration step using a small-pore filter of, e.g., about 70 microns or about 40 microns, for removing additional contaminants such as collagen fibers. Because the minced and/or enzymatically digested tissue is generally viscous, the tissue can be washed or diluted with an appropriate sterile solution (such as a buffered salt solution) at any stage in the process. For example, after the minced and/or enzymatically digested tissue has been separated from the undigested tissue following the first filtration step, further washes can be performed to further cleanse the minced and/or enzymatically digested tissue before the second filtration step. Following multiple rounds of filtration, target cells substantially free of tissue sample can be collected by sedimentation.

Figure 10A:
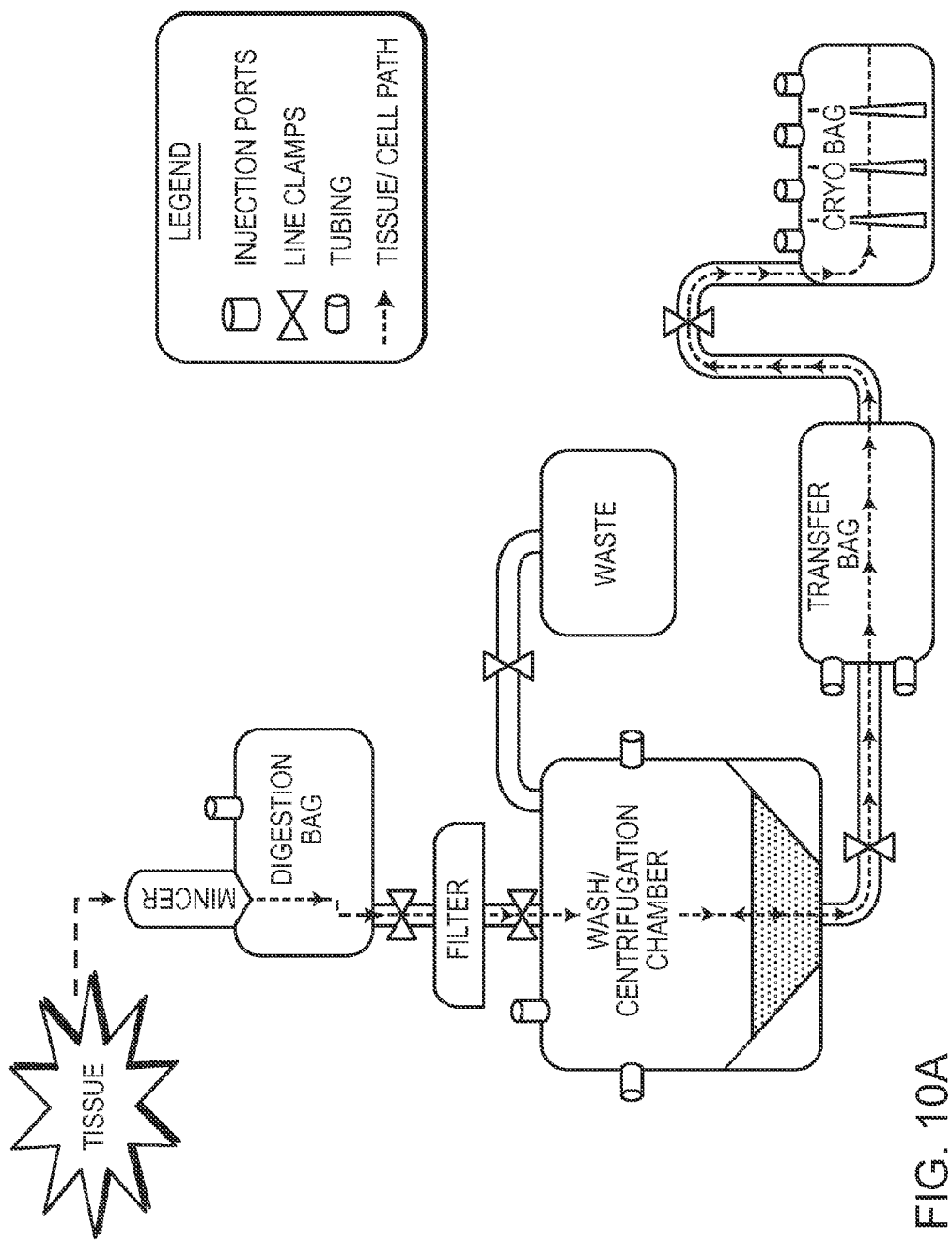
FIGS. 10A-10G depict procedures for collecting and isolating desired cells from a tissue sample.

FIG. 10A depicts an exemplary procedure for collecting and isolating desired cells from a tissue sample. The tissue sample may be initially placed within a compartment, where it can be minced, parsed, or separated into smaller portions. An advantage of mincing the tissue sample before any enzymatic digestion is that the entire surface area of the tissue sample on which the enzyme can act is increased. The compartment may be fitted and attached to one port (e.g., an aperture) of a container (e.g., digestion bag) such that a tissue sample introduced into the compartment can directly pass through into the container. The compartment may or may not be removably attached to the container.

The container defines a sterile, sealed interior space that holds the minced tissue sample and fluids. The container may include sealed ports for introducing or dispensing materials and fluids into or from the container. For example, the container may include one or more injection ports for introducing fluids and one or more withdrawal ports for dispensing or suction fluids and materials from the container. Further, in an alternative embodiment, each of the injection ports and withdrawal port can be configured such that fluids and materials can only be moved in one direction to and from the container. Moreover, the ports can be disposed at an opposite end of the container from the compartment, though the ports can also be disposed along any portion of the perimeter of the container. In an embodiment, the ports are not removably secured to the container. Additionally or alternatively, syringes, air vents, capped air vents, or other devices that mate with a luer connection can be attached to the ports. All ports may be swabbable so that sterility is maintained.

Subsequently, the minced tissue can optionally be digested by, for example exposing it to a chemical or an enzyme. In an embodiment, the minced tissue may be digested by an enzyme, for example, a protease, such as a collagenase, hyaluronidase, or dispase, separately or in combination. The enzyme may be directly introduced into the container, such that the enzyme digests the minced tissue. For example, a syringe, or any other device that can house fluids, materials, or air, can be connected to the container (e.g., via a luer connection) and used to dispense, for example, a protease into the container to digest the minced tissue sample. To enhance digestion of the minced tissue sample, the container can be inverted to circulate the enzyme about the container. Depending on the rate of enzymatic breakdown of the minced tissue sample, the container can be placed at rest and the minced tissue sample can be incubated with the enzyme at 37° C. for a period of time, for example, for about one to three hours, though more or less time is contemplated, to digest the minced tissue sample. Additionally or alternatively, to assist in the incubation process, the container can optionally be periodically mixed with an orbital shaker or moved through a series of rollers or other compression-type device to assist in the break-down of the minced tissue sample within the container. In an example in which the tissue sample is about 10 mL, a user can inject about 10 mL of enzyme into the container, though more or less enzyme is contemplated. Once the minced tissue sample is digested, a digested tissue sample of about 20-30 mL results.

Before the cells are separated from the minced and/or enzymatically digested tissue, any remaining fragments of undigested tissue are optionally removed to facilitate the subsequent purification of the cells. Depending on their size, undigested tissue can be removed by, for example, physical extraction, decanting, aspiration, sedimentation, or preferably, filtering. Optionally, the undigested tissue that is removed may be stored and/or used for other purposes such as a seeding source for the expansion of stem cells.

FIGS. 10A-10D illustrate various embodiments in which separation is achieved by filtration. Specifically, FIGS. 10A-10D depict a fluid passageway that connects the container holding the digested tissue sample to a filter unit which can be removably attached to the container. The filter unit may use a single filter, or a plurality of filters, optionally of decreasing size. Alternatively, a filter may be fitted and disposed in the container such that that the container is divided into two sub-spaces. The filter may be symmetrically or asymmetrically placed within the container. Additionally or alternatively, the filter may be fitted within a port, for example, a withdrawal port. The size of the filter can be about 500 microns, about 250 microns, about 150 microns, about 100 microns, about 70 microns, about 40 microns, or any range thereof, depending on the application. The digested tissue sample, which can be viscous, may be diluted prior to filtering so that the resultant tissue sample can more easily move through the filter into downstream containers or components for further processing. Examples of diluting solutions include phosphate buffered saline (PBS), 5% human serum albumin, saline, heta-starch, and fresh plasma (e.g., autologous plasma). In an embodiment, a syringe, or any other device that can house fluids, is used to dispense a diluting solution into the container via an injection port. In an example in which the digested tissue sample is about 20-30 mL, a user can inject about 250 mL of a diluting solution into the container, though more or less solution is contemplated. As a result, the container holds about 250-300 mL of a diluted, digested tissue sample. Following filtration, the eluate may be propelled, e.g., by vacuum, suction, or gravity, into a second sterile container (e.g., a wash/centrifugation bag) via a fluid passageway preferably regulated by line clamps (e.g., butterfly line clamps).

Isolating cells from diluted, minced and/or enzymatically digested tissue can be accomplished by various mechanisms. In an embodiment, the target cells are isolated from the diluted, minced and/or enzymatically digested tissue by sedimentation. Although gravity sedimentation can be used, the sedimentation process can be accelerated by, for example, centrifugation. The present invention can include customized centrifuge buckets, inserts, and balance weights to ensure proper centrifuge of the system.

Sedimentation separates the target cells from the diluted, minced and/or enzymatically digested tissue sample. To facilitate cell collection, supernatants substantially free of cells are optionally removed via an outlet port and a fluid passageway preferably regulated by line clamps. The supernatant may be removed by, for example, decanting or aspiration. In an example in which the second sterile container is a compressible bag, the supernatant may be decanted by physically pressing the bag. Alternatively, the supernatant may be removed, e.g., by vacuum, suction, or gravity. Optionally, the supernatant can be removed into a waste container that is connected to the second sterile container through an outlet port and a fluid passageway regulated by line clamps. In an embodiment, the removed supernatant may be stored and/or used for other purposes such as maintaining cells (in culture).

Figure 10B:
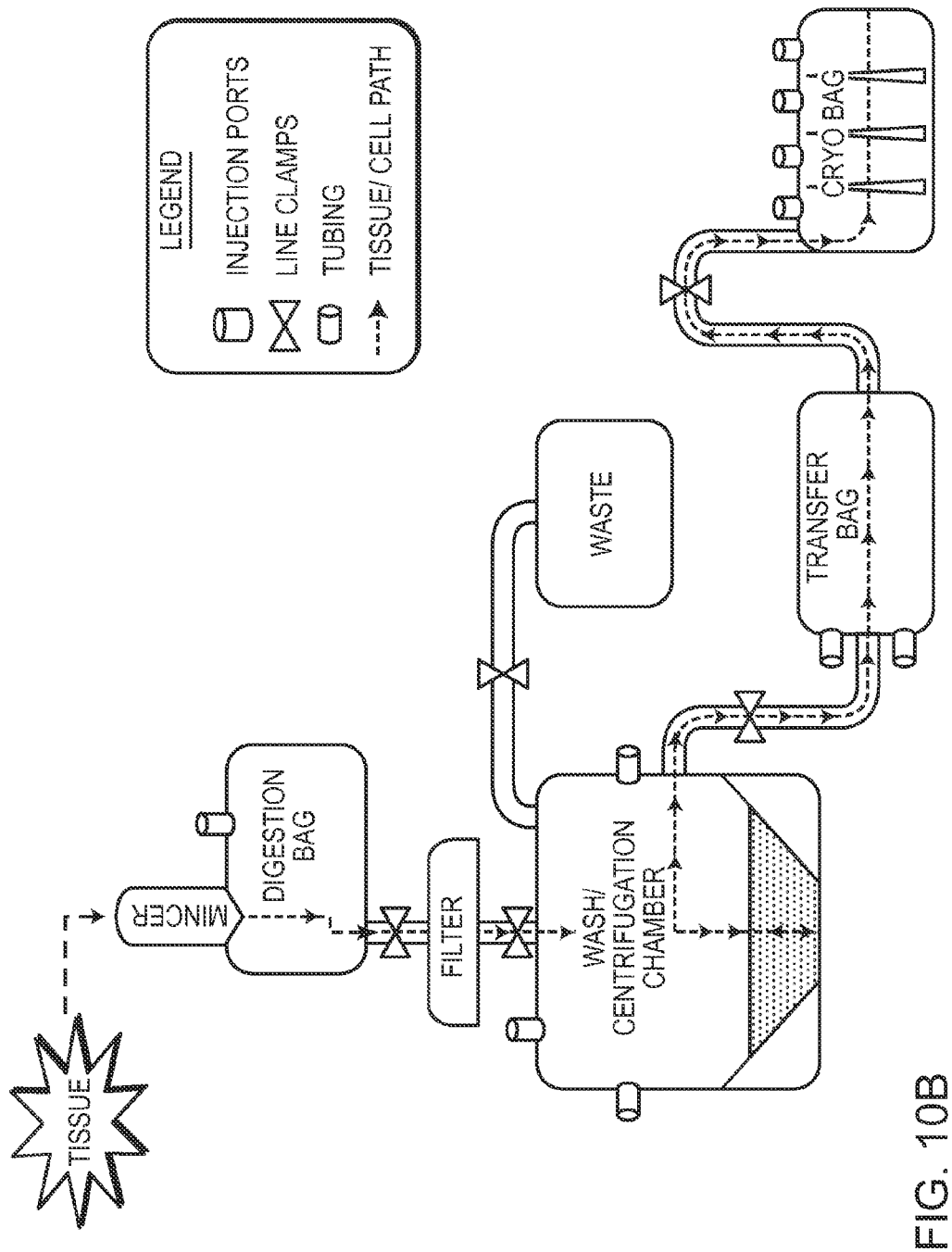

To collect target cells, a small volume of a diluting solution (e.g., 20 ml of autologous plasma) can be added to resuspend the cell pellet which may collect at the bottom of the second sterile container. As shown in the embodiment depicted in FIG. 10A, the second sterile container can have a bottom that is tapered to an angle sufficient to facilitate movement of the target cells into a fluid passageway located at the bottom of the container, and optionally into a transfer container (e.g., transfer bag). Alternatively, as depicted in FIG. 10B, target cells may be moved into a fluid passageway located at the side of the container, and optionally into a transfer container. Movement of the cells out of the second sterile container and into the fluid passageway and optionally into a transfer container can be facilitated by vacuum or suction and may be regulated by line clamps.

If needed, the purified, target cells can be used immediately. Typically, however, the cells are cryopreserved for later use. To achieve long-term storage, cells can be transferred from the optional transfer container into a sealable, sterile container amenable to freezing (e.g., cryo-bag). Alternatively, cells can be directly collected from the second sterile container into a freezable container for later use. Cryoprotectants are added to assist in storage and preservation of target cells, and can include, for example, dimethyl sulfoxide (DMSO), albumin, and/or dextran, separately or in combination. Cryoprotectants may be added to the cells within the second sterile container following sedimentation. Alternatively, cryoprotectants may be added to and mixed with the cells within the optional transfer container or within the freezable container for long-term storage and later use.

Figure 10C:
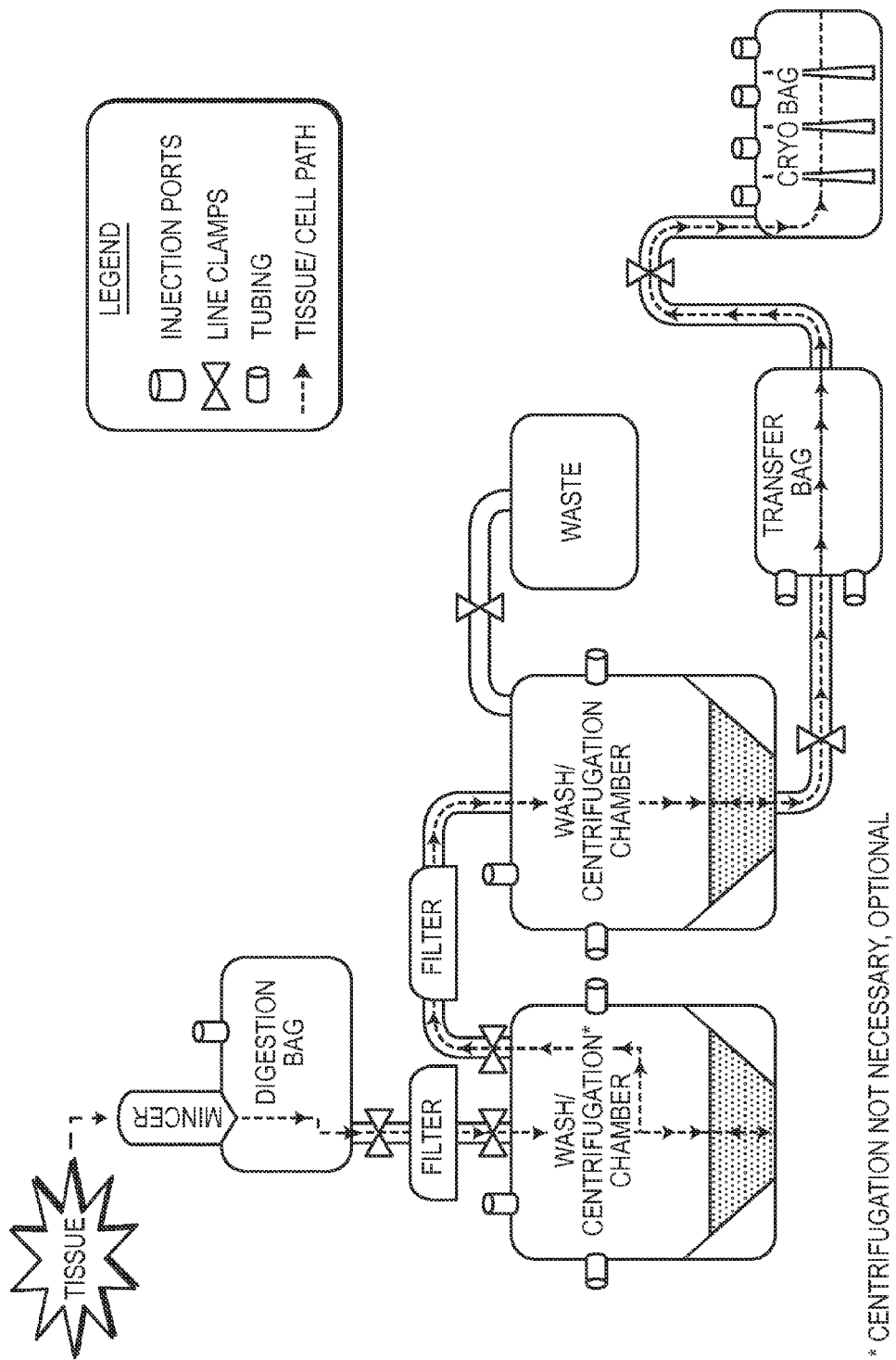
Figure 10D:
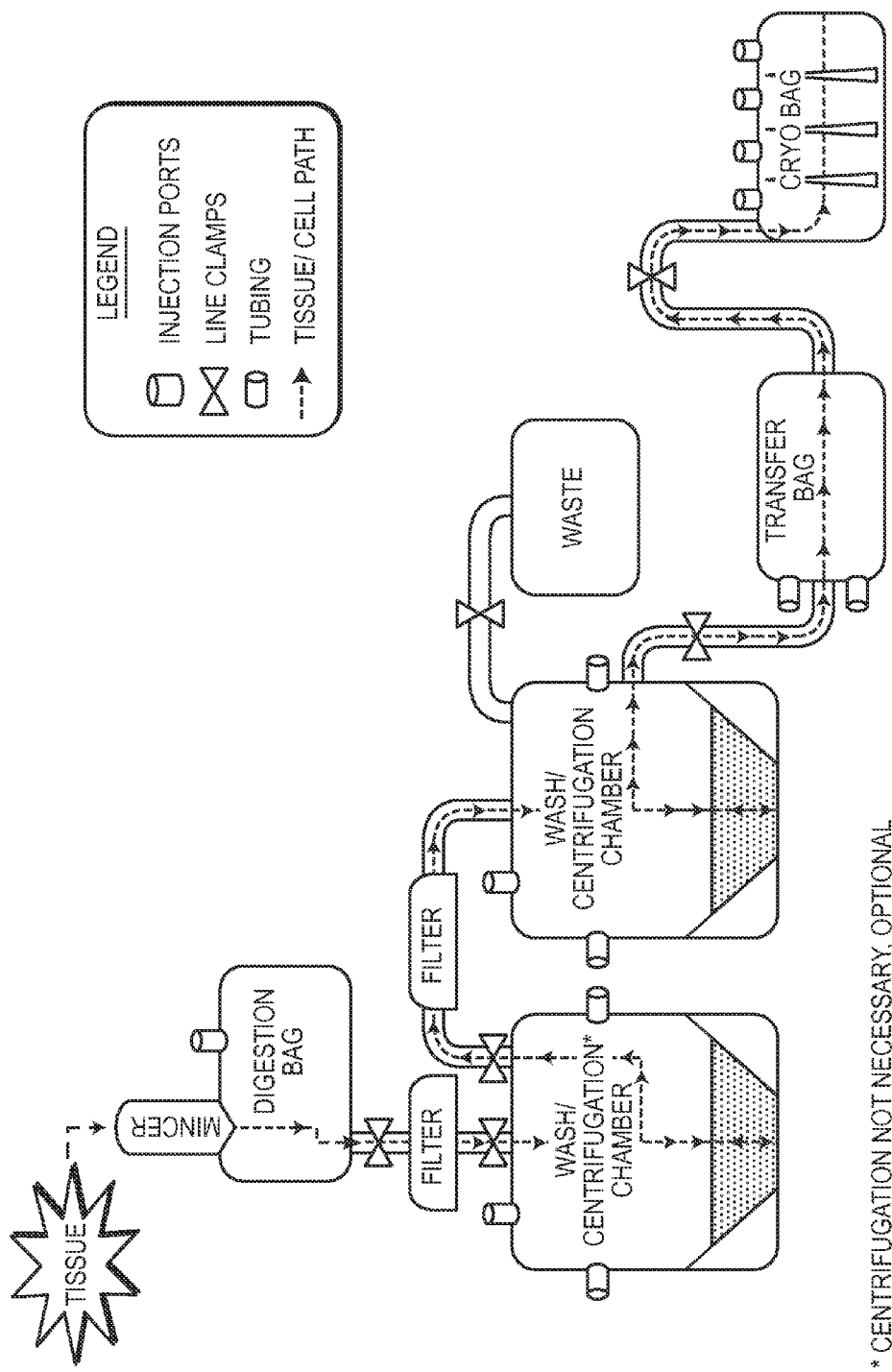

In an embodiment, methods for separating minced and/or enzymatically digested tissue from undigested tissue may include two or more filtration steps as depicted in FIGS. 10C-10D. For example, minced and/or enzymatically digested tissue may be subjected to a first filtration step to remove coarse, undigested tissue. Because the minced and/or enzymatically digested tissue is generally viscous, the tissue can be washed or diluted with an appropriate sterile solution at any stage in the process. For example, after the minced and/or enzymatically digested tissue has been separated from the undigested tissue following the first filtration step, further washes can be performed to further cleanse the tissue prior to a second filtration step. In an embodiment, the second filtration step may utilize a smaller sized filter in order to remove contaminants such as collagen fibers from the minced and/or enzymatically digested tissue. Following the second filtration step, target cells may be collected by sedimentation and moved into an optional transfer bag through a fluid passageway located either at the bottom of the container (FIG. 10C) or at the side of the container (FIG. 10D). Alternatively, the cells may be directly collected into a sterile cryo-bag for long-term storage and later use.

Figure 10E:
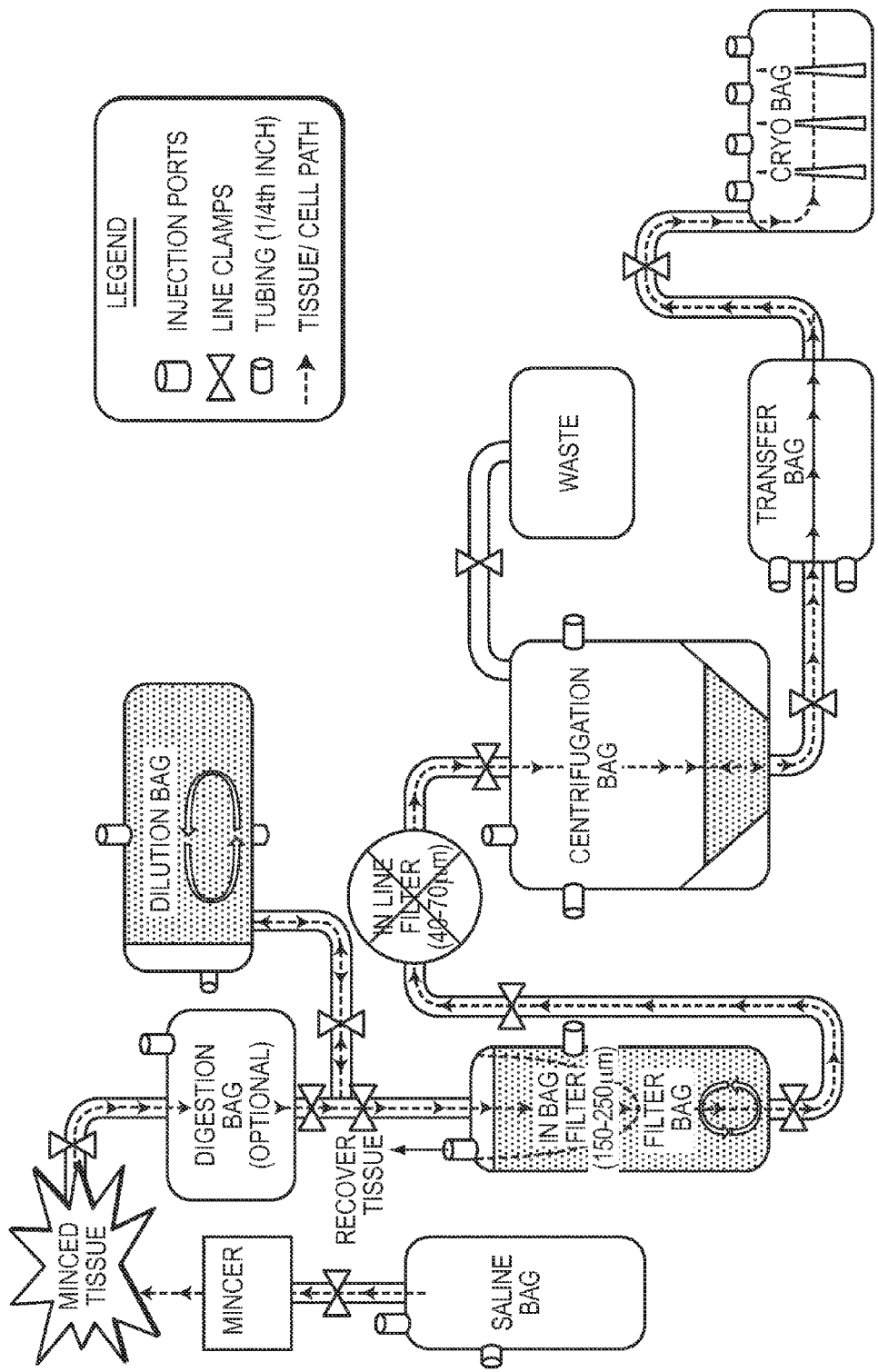
Figure 10F:
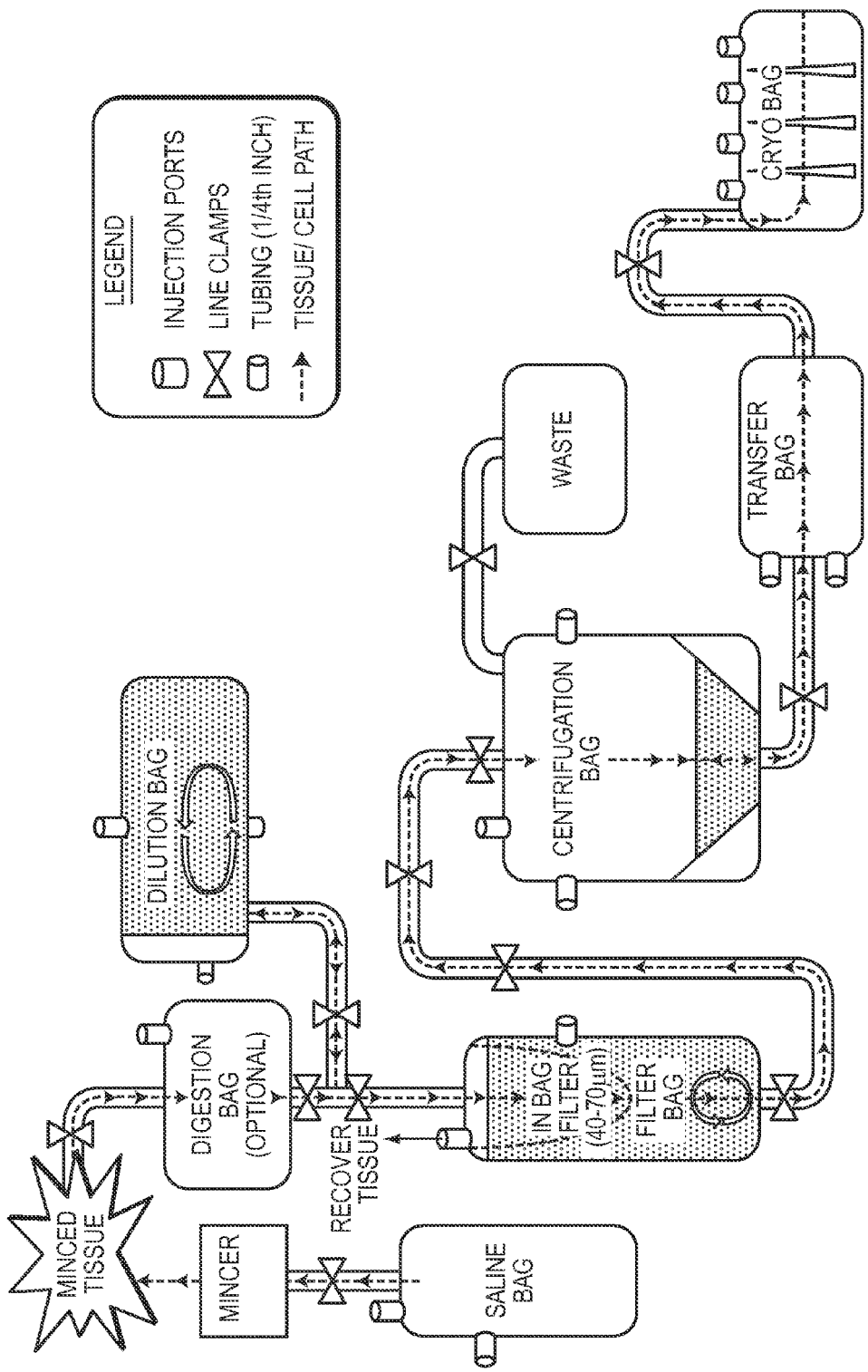
Figure 10G:
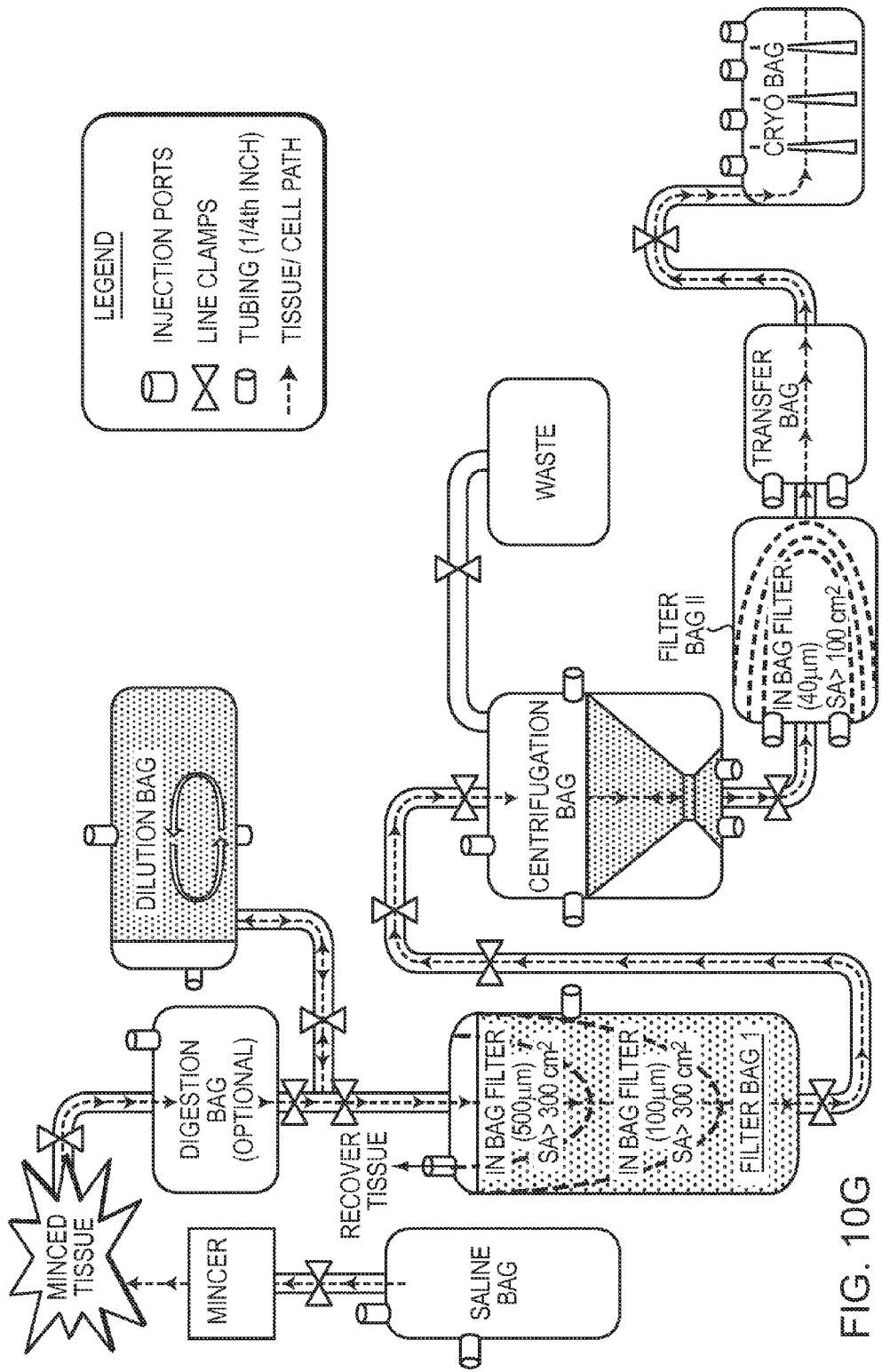

Additional exemplary processes for separating minced tissue samples are depicted in FIGS. 10E-10G. In each of these processes, a tissue sample is placed in a mincer, such as the mincer of FIG. 7. In operation, the mincer forces the tissue sample through one or more cutting surfaces and deposits the finely minced tissue on the other side of the cutting surface(s). A saline bag is provided to permit the flushing of the tissue out of the mincer; typically, up to 500 mL of saline may be used for this purpose. When flushed from the mincer, the minced tissue may flow into an optional digestion bag (as shown), where the minced tissue may be enzymatically digested (as described with reference to FIGS. 10A-10D) prior to further processing. The optional digestion bag is in fluid communication with a dilution bag. Alternatively, if the mechanical mincing has obviated the need for any enzymatic digestion, the minced tissue can flow directly into a dilution bag. The mechanically minced tissue (whether or not subjected to enzymatic digestion) may be viscous. The dilution bag can be mechanically manipulated to encourage the mixing of the tissue and the saline. The dilution bag is also fitted with an optional injection port, permitting the injection of additional saline into the dilution bag as required.

The tissue suspension is then filtered, once the viscosity has been sufficiently reduced. As shown in FIGS. 10E-G, the suspension passes from the dilution bag into a filter bag having at least one in-bag filter. FIG. 10E depicts an embodiment with a single in-bag filter which retains particles larger than about 40-70 µm. FIG. 10F depicts an embodiment with a single in-bag filter which retains particles larger than about 150-250 µm. In FIG. 10F, the filtrate from the in-bag filter then passes through a second, in-line filter unit which retains particles larger than about 40-70 µm. FIG. 10G depicts an embodiment in which the filter bag contains two in-bag filters in succession, each in-bag filter having a surface area of at least 300 cm$^2$; the first filter retains particles larger than about 500 µm and the second filter retains particles larger than about 100 µm. In each of FIGS. 10E-G, the filter bag includes a port permitting the removal of the retentate from the first filter. This retentate can optionally be used as a tissue explant for culturing cells.

The filtrates in FIGS. 10E-G pass into a centrifugation bag like those depicted in FIGS. 10A-D. Cells are separated from the suspension by sedimentation (e.g. by centrifugation) and are concentrated in the bottom portion of the bag, or in a fluid passageway connected to the bottom portion of the bag. The supernatant can be removed (e.g. by decanting, aspiration, vacuum, suction, or by compressing the bag) through tubing optionally connected to a waste container. The supernatant may be used for other purposes such as maintaining cells in culture.

To collect target cells, a small volume of a diluting solution (e.g., 20 ml of autologous plasma) can be added to resuspend sedimented cells. As shown in FIGS. 10E-G, the resuspended cells can pass from the centrifugation bag into a transfer bag, optionally after passing through a second filter bag, such as a second filter bag containing a filter having a surface area of at least 100 cm² and retaining particles greater than about 40 µm, as shown in FIG. 10G. The cells can be transferred to a cryobag and one or more cryoprotectants can be added, such as DMSO, albumin, and/or dextran, as described above for FIGS. 10A-D.

The methods described herein are effective for purifying cells from a variety of solid tissues. For example, the methods described herein can separate cells, such as stem cells, from fat tissue or afterbirth tissue, such as placenta or umbilical cord tissue or, more specifically, a tissue comprising Wharton's Jelly. The purified Wharton's Jelly stem cells can be used to treat or regenerate any of a variety of tissues such as bone, cartilage, fat or muscle. These cells can also facilitate hematopoietic engraftment and have the potential to regulate and suppress immune responses in a host.

In addition to purified cells, the methods described herein also yield additional useful products. For example, when the cells are separated from the minced and/or enzymatically digested tissue, the remaining, cell-depleted tissue is a rich, sterile solution that can be used for maintaining cells (in culture, for example). Further, any fragments of undigested tissue remaining after a digestion process can also be useful. For example, undigested umbilical cord tissue can be utilized as a seeding source for the expansion of mesenchymal stem cells.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive. Furthermore, the configurations described herein are intended as illustrative and in no way limiting. Similarly, although physical explanations have been provided for explanatory purposes, there is no intent to be bound by any particular theory or mechanism, or to limit the claims in accordance therewith.

INCORPORATION BY REFERENCE

The entire disclosures of each of the patent documents and scientific articles cited herein are incorporated by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A tissue mincing tool comprising:
a compartment for a tissue sample;
a solid member automatedly translatable within the compartment;
a cutting surface at one end of the compartment; and
a sterile, sealed container,
wherein the compartment is arranged to position the tissue sample between the solid member and the cutting surface,
and further wherein the cutting surface separates the compartment from the sterile, sealed container, such that a tissue sample that is pressed, via an automated translation of the solid member, into contact with and through the cutting surface is deposited as a minced tissue within the sterile, sealed container.

2. The tissue mincing tool of claim 1, wherein the cutting surface comprises an automated cutting system.

3. The tissue mincing tool of claim 2, wherein the automated cutting system comprises semi-automatic scissors.

4. The tissue mincing tool of claim 1, wherein the cutting surface is dimensioned to mince the tissue sample into fragments having an average cross-section no greater than four square millimeters.

5. The tissue mincing tool of claim 1, wherein the cutting surface is dimensioned to mince the tissue sample into fragments, and further comprising a second cutting surface for reducing an average cross-section of the fragments.

6. The tissue mincing tool of claim 1, further comprising at least one mincer screen positioned in proximity to the cutting surface.

7. The tissue mincing tool of claim 6, wherein the at least one mincer screen is moveable towards the tissue sample.

8. The tissue mincing tool of claim 1, further comprising a suction cup for stabilizing the tissue mincing tool during operation thereof.

9. The tissue mincing tool of claim 1, wherein the sterile, sealed container comprises at least one sealed access port permitting the sterile introduction of a fluid into the container.

10. The tissue mincing tool of claim 1, wherein an interior surface of the compartment is threaded.

11. The tissue mincing tool of claim 1, further comprising a gasket for sealing the compartment.

12. The tissue mincing tool of claim 1, wherein a portion of the compartment near its end has a substantially constant cross-section.

13. The tissue mincing tool of claim 12, wherein the solid member is shaped to mate with and to fill the portion of the compartment.

14. The tissue mincing tool of claim 1, wherein the cutting surface is rotatable.

15. The tissue mincing tool of claim 1, wherein the cutting surface is moveable towards the tissue sample.

16. The tissue mincing tool of claim 1, further comprising a shaft crank for moving the cutting surface towards the tissue sample.

17. The tissue mincing tool of claim 1, further comprising a shaft crank for actuating the cutting surface, the shaft crank configured for automatic machine actuation.

18. The tissue mincing tool of claim 1, wherein the tissue mincing tool comprises a series of cutting surfaces at the one end of the compartment.

19. A method of mincing a tissue sample, the method comprising:
automatically translating the solid member to press the tissue sample into contact with and through the cutting surface of the tissue mincing tool according to claim 1.

20. The method of claim 19, wherein the cutting surface comprises an automated cutting system.

21. The method of claim 20, wherein the automated cutting system comprises semi-automatic scissors.

22. The method of claim 19, further comprising automatically machine-actuating the cutting surface.

23. The method of claim 22, wherein the cutting surface is automatically machine-actuated via an automatic machine-actuation of a shaft crank coupled thereto.

24. A method of digesting a tissue sample, the method comprising:
   mincing the tissue sample according to the method of claim 19 and, optionally, transferring the minced tissue to a second sterile, sealed container; and
   injecting an enzyme, whereby the enzyme digests the minced tissue.

25. The method of claim 24, wherein the enzyme is a collagenase.

26. A method of separating cells from a tissue sample, the method comprising:
   mincing the tissue sample according to the method of claim 19; and
   removing undigested tissue.

27. The method of claim 26, further comprising diluting the tissue sample, wherein the undigested tissue is subsequently removed by filtering.

28. The method of claim 27, further comprising sedimenting a filtrate generated by the filtering.

29. The method of claim 28, further comprising re-suspending sedimented cells and filtering the re-suspended sedimented cells.

30. The method of claim 19, wherein the tissue sample comprises Wharton's Jelly stem cells.

\* \* \* \* \*